United States Patent
Phillips

(10) Patent No.: US 12,349,996 B2
(45) Date of Patent: Jul. 8, 2025

(54) ROBOTIC JOINT CONTROL

(71) Applicant: CMR SURGICAL LIMITED, Cambridge (GB)

(72) Inventor: Desmond Phillips, Cambridge (GB)

(73) Assignee: CMR SURGICAL LIMITED, Cambridge (GB)

( * ) Notice: Subject to any disclaimer, the term of this patent is extended or adjusted under 35 U.S.C. 154(b) by 928 days.

(21) Appl. No.: 17/080,916

(22) Filed: Oct. 27, 2020

(65) Prior Publication Data
US 2021/0121255 A1 Apr. 29, 2021

(30) Foreign Application Priority Data
Oct. 29, 2019 (GB) ..................................... 1915688

(51) Int. Cl.
*A61B 34/35* (2016.01)
*A61B 34/30* (2016.01)
(Continued)

(52) U.S. Cl.
CPC .............. *A61B 34/35* (2016.02); *A61B 34/30* (2016.02); *A61B 90/06* (2016.02); *B25J 9/1643* (2013.01);
(Continued)

(58) Field of Classification Search
CPC ... A61B 34/35; A61B 90/06; A61B 2034/305; A61B 2090/061; A61B 2090/066;
(Continued)

(56) References Cited

U.S. PATENT DOCUMENTS

| | | | |
|---|---|---|---|
| 9,981,381 B1 | 5/2018 | Nagarajan | |
| 2011/0218673 A1 | 9/2011 | Oga et al. | |
| (Continued) | | | |

FOREIGN PATENT DOCUMENTS

| | | |
|---|---|---|
| CN | 104781050 A | 7/2015 |
| CN | 106456265 A | 2/2017 |
| (Continued) | | |

OTHER PUBLICATIONS

Indian Examination Report from correspondong Indian Application No. 202217029944 dated Sep. 30, 2022.
(Continued)

*Primary Examiner* — Khoi H Tran
*Assistant Examiner* — Sarah A Tran
(74) *Attorney, Agent, or Firm* — Lando & Anastasi, LLP

(57) ABSTRACT

A system comprising: a robot comprising an arm having an attachment and, for each of n joints, a driver and a joint sensor; and a control unit configured to: obtain a desired position of the attachment; for each of k<n joints, obtain a sensed joint state; compare the states to a set of criteria indicative of the arm moving from a first to a second configuration; the states matching the set of criteria, determine a magnitude of an adjustment signal configured to slow, halt or reverse movement of the arm towards the second configuration; using the desired position of the attachment and the states, determine a direction of the adjustment signal; for each of the n joints, obtain a sensed joint state; using the desired position of the attachment, the obtained n states and the adjustment signal, determine signals for controlling the drivers; and drive the joints using the signals.

19 Claims, 6 Drawing Sheets

(51) Int. Cl.
  *A61B 90/00* (2016.01)
  *B25J 9/16* (2006.01)
  *G16H 20/40* (2018.01)
  *G16H 40/63* (2018.01)

(52) U.S. Cl.
  CPC ............. *G16H 20/40* (2018.01); *G16H 40/63* (2018.01); *A61B 2034/305* (2016.02); *A61B 2090/061* (2016.02); *A61B 2090/066* (2016.02); *A61B 2090/067* (2016.02); *B25J 9/1633* (2013.01); *B25J 9/1653* (2013.01)

(58) Field of Classification Search
  CPC ...... A61B 2090/067; A61B 2034/2059; A61B 34/74; A61B 34/76; A61B 34/30; A61B 34/00; A61B 34/20; A61B 34/70; A61B 90/00; A61B 2034/2046; A61B 2090/00; A61B 2090/06; A61B 2090/064; G16H 20/40; G16H 40/63; G16H 20/00; G16H 40/00; G16H 40/60; B25J 9/1643; B25J 9/1651; B25J 9/00; B25J 9/16; B25J 9/1628; B25J 9/1633; B25J 9/1653; G05B 2219/40333; G05B 2219/40367; G05B 2219/40371; G05B 2219/45117; G05B 2219/00; G05B 2219/30; G05B 2219/40; G05B 2219/45
  USPC ........................................................ 700/245
  See application file for complete search history.

(56) References Cited

U.S. PATENT DOCUMENTS

| | | | | |
|---|---|---|---|---|
| 2014/0039681 A1* | 2/2014 | Bowling | ................ | A61B 34/30 700/261 |
| 2014/0081461 A1* | 3/2014 | Williamson | ........... | B25J 9/1643 700/261 |
| 2014/0358161 A1* | 12/2014 | Hourtash | ............... | B25J 9/1607 901/15 |
| 2019/0060008 A1 | 2/2019 | Bailey et al. | | |
| 2019/0105117 A1* | 4/2019 | Brisson | .................. | A61B 34/30 |
| 2020/0368861 A1* | 11/2020 | Artigas | ................. | B62D 65/00 |

FOREIGN PATENT DOCUMENTS

| | | |
|---|---|---|
| CN | 107072864 A | 8/2017 |
| CN | 108882966 A | 11/2018 |
| WO | 2014043702 A1 | 3/2014 |
| WO | 2015142796 A1 | 9/2015 |
| WO | 2019094794 A2 | 5/2019 |

OTHER PUBLICATIONS

United Kingdom Search Report from corresponding United Kingdom Application No. GB1915688.4 dated Apr. 17, 2020.
Christian Scheurer et al: "Industrial implementation of a multi-task redundancy resolution at velocity level for highly redundant mobile manipulators", Robotics in the era of digitalisation: 47th International Symposium on Robotics: Jun. 21-22, 2016, Messe Munchen, Entrance East, Munich, Germany, Jun. 21, 2016 (Jun. 21, 2016), pp. 109-117, XP055525840, DE, ISBN: 978-3-8007-4231-8.
Notification of Transmittal of the International Search Report and the Written Opinion of the International Searching Authority from corresponding PCT/GB2020/052714 dated Feb. 2, 2021.
Stefano Chiaverini et al: "Part A—Chapter 10. Redundant Robots" In: "Springer Handbook of Robotics", Jul. 27, 2016 (Jul. 27, 2016), Springer International Publishing, Cham, XP055767312, ISBN: 978-3-319-32552-1, pp. 221-242.
United Kingdom Examination Report from corresponding United Kingdom Application No. GB1915688.4 dated Sep. 15, 2023.
Chinese Office Action from corresponding Chinese Application No. 202080075837.6 dated Mar. 31, 2025.

* cited by examiner

ROBOTIC JOINT CONTROL

CROSS-REFERENCE TO RELATED APPLICATION

This application claims the benefit under 35 U.S.C. § 119 of United Kingdom Patent Application No. 1915688.4 filed on Oct. 29, 2019 which is hereby incorporated herein by reference in its entirety for all purposes.

FIELD OF THE INVENTION

This invention relates to the control of joints in robotic systems such as robot arms, and in particular to the control of redundant robot arms operating with one or more constraints.

BACKGROUND

A typical robotic manipulator comprises a series of rigid elements which are coupled together by joints. The elements may be joined in series to form an arm. The joints can be driven so as to cause relative motion of the rigid elements. The rigid elements may stem from a base and terminate in an attachment for an instrument or end effector. Thus motion at the joints can be used to position the end effector at a desired location. Each joint may provide rotational motion or linear motion. The joints may be driven by any suitable means, for example electric motors or hydraulic actuators.

During operation, the robot may be required to cause the end effector to move to a desired position. For example, the robot may be required to use the end effector to pick up an object. This requires the end effector to be moved to where the object is. To accomplish this, some combination of motions of the joints is required. A control system of the robot is used to calculate those motions.

Conventionally, a robot is provided with position sensors, each of which senses the configuration of a respective one of the joints. This position information is fed to the control system.

A known strategy for the control system is as follows:
1. Receive information indicating a desired position of the end effector.
2. Determine a set of target configurations of the joints of the robot that will result in the end effector being in that position. This is known as inverse kinematics.
3. Receive information indicating the current configuration of each joint in the robot, compare those current configurations to the target configurations and calculate a set of torques or forces required at each joint in order to reduce the error between the respective joint's current and target positions.
4. Send drive signals to the actuators in the robot in order to impose those torques or forces at the respective joints.

This series of steps is performed repetitively so that over time the motion of the robot conforms to the target configurations.

This approach is problematic because typically the inverse kinematics problem is considered hard to solve. One reason for this is that certain poses of the manipulator can become singular, meaning that it is impossible to make subsequent movements of the end effector in all directions with finite joint velocities. Another reason is that, in moving from one position of the end effector to another, the manipulator may attempt to move through a configuration that is undesirable, for example because it would cause a collision with another manipulator or object within the manipulator's workspace.

There is a need for an improved control system for mechanical systems such as robot manipulators.

SUMMARY

This summary is provided to introduce a selection of concepts that are further described below in the detailed description. This summary is not intended to identify key features or essential features of the claimed subject matter, nor is it intended to be used to limit the scope of the claimed subject matter.

According to an aspect of the present invention there is provided a robotic system comprising:
  a robot having a base and an arm extending from the base to an attachment for an instrument, the arm comprising n joints, where n>1, whereby the configuration of the arm can be altered, the arm having a plurality of configurations for a given relationship between the base and the attachment for the instrument, the robot comprising a driver for each joint configured to drive the joint to move and a joint sensor for each joint for sensing a state of the joint; and
  a control unit configured to:
    obtain a desired position of the attachment for the instrument;
    for each of k joints where k<n, obtain a sensed joint state;
    compare the obtained k sensed joint states to a set of constraint criteria, the set of constraint criteria being indicative of the arm moving from a first configuration towards a second configuration, where movement of the arm is more constrained in the second configuration than in the first configuration;
    where the obtained k sensed joint states match the set of constraint criteria, determine a magnitude of an adjustment signal configured to slow, halt or reverse movement of the arm towards the second configuration;
    using the desired position of the attachment for the instrument and the obtained k sensed joint states, determine a direction of the adjustment signal;
    for each of the n joints, obtain a sensed joint state;
    using the desired position of the attachment for the instrument, the obtained n sensed joint states and the adjustment signal, determine a set of control signals for controlling the drivers; and
    drive the joints using the set of control signals.

The control unit may be configured to determine the adjustment signal in dependence on one or more of: an instrument to be attached to the arm, a procedure that the arm is configured to perform, usage data gathered from system telemetry, and one or more algorithms for data analytics. The set of constraint criteria may comprise a range of values bounded by upper and lower threshold values, and the control unit may be configured to determine that the k sensed joint states match the set of constraint criteria where the k sensed joint states comprise a value that equals one or other of the upper and lower threshold values or is between the upper and lower threshold values. The control unit may be configured to calculate a difference value from the difference between one of the k sensed joint state values and one or other of the upper and lower threshold values, and to determine the adjustment signal using the difference value. Determining the adjustment signal may comprise applying a gain factor to the difference value. The gain factor may be selected in dependence on one or more of the characteristics of the arm, an instrument to be attached to the arm, the environment of the arm, and the procedure that the arm is used to perform.

The set of constraint criteria may comprise a plurality of ranges of values, in respect of a plurality of joints, bounded by respective upper and lower threshold values, and the control unit may be configured to determine that the k sensed joint states match the set of constraint criteria where respective sensed joint states comprise values that equal one or other of the respective upper and lower threshold values or are between the respective upper and lower threshold values.

The adjustment signal may be configured to adjust a plurality of joints of the arm. The second configuration may be relatively more constrained due to one or more of: limiting a range of motion about a joint; approaching or causing a joint singularity; approaching a joint rotation limit of a joint; and proximity of the arm to a person and/or an object.

The control unit may be configured to gate the adjustment signal in dependence on movement of the attachment for the instrument. The adjustment signal may comprise a joint speed signal. The control unit may be configured to filter the adjustment signal and to determine the set of control signals using the filtered adjustment signal. The control unit may be configured to dynamically modify the set of constraint criteria and/or the gain factor.

The state of a joint may comprise one or more of an angle of that joint, a position of that joint, a speed or velocity of that joint, an acceleration of that joint, and a torque on or about that joint. The control unit may be configured to determine the adjustment signal such that the adjustment signal does not cause relative movement between the base and the attachment for the instrument. The control unit may be configured to determine the set of constraint criteria in dependence on an operating mode of the robotic system.

The control unit may be configured to use the desired position of the attachment for the instrument and the obtained k sensed joint states to determine a solution for the k joints, and to use the solution for the k joints to determine the direction of the adjustment signal. The control unit may be configured to determine the solution for the k joints by using a least-squares method or variation thereof and determining a minimum norm solution for the k joints that lies within the nullspace.

According to another aspect of the present invention there is provided a computer-implemented method of controlling a robotic system, the robotic system comprising a robot having a base and an arm extending from the base to an attachment for an instrument, the arm comprising n joints, where n>1, whereby the configuration of the arm can be altered, the arm having a plurality of configurations for a given relationship between the base and the attachment for the instrument, the robot comprising a driver for each joint configured to drive the joint to move and a joint sensor for each joint for sensing a state of the joint; the method comprising:

obtaining a desired position of the attachment for the instrument;

for each of k joints where k<n, obtaining a sensed joint state;

comparing the obtained k sensed joint states to a set of constraint criteria, the set of constraint criteria being indicative of the arm moving from a first configuration towards a second configuration, where movement of the arm is more constrained in the second configuration than in the first configuration;

where the obtained k sensed joint states match the set of constraint criteria, determining a magnitude of an adjustment signal configured to slow, halt or reverse movement of the arm towards the second configuration;

using the desired position of the attachment for the instrument and the obtained k sensed joint states, determining a direction of the adjustment signal;

for each of the n joints, obtaining a sensed joint state;

using the desired position of the attachment for the instrument, the obtained n sensed joint states and the adjustment signal, determining a set of control signals for controlling the drivers; and driving the joints using the set of control signals.

The method may comprise determining the adjustment signal in dependence on one or more of: an instrument to be attached to the arm, a procedure that the arm is configured to perform, usage data gathered from system telemetry, and one or more algorithms for data analytics. The set of constraint criteria may comprise a range of values bounded by upper and lower threshold values, and the method may comprise determining that k sensed joint states match the set of constraint criteria where the k sensed joint states comprise a value that equals one or other of the upper and lower threshold values or is between the upper and lower threshold values. The method may comprise calculating a difference value from the difference between one of the k sensed joint state values and one or other of the upper and lower threshold values, and determining the adjustment signal using the difference value.

According to another aspect of the present invention there is provided a control unit for a robotic system configured to perform the method as described herein.

According to another aspect of the present invention there is provided a robotic system comprising a robot having a base and an arm extending from the base to an attachment for an instrument, and a control unit configured for controlling the arm by the method as described herein.

According to another aspect of the present invention there is provided a non-transitory computer readable storage medium having stored thereon computer readable instructions that, when executed at a computer system, cause the computer system to perform the method as described herein.

Any feature of any aspect described herein may be combined with any other feature of any aspect described herein. Any apparatus feature may be rewritten as a method feature, and vice versa.

These are not written out in full merely for the sake of brevity.

BRIEF DESCRIPTION OF THE DRAWINGS

The present invention will now be described by way of example with reference to the accompanying drawings.

In the drawings.

DETAILED DESCRIPTION

Figure 1:
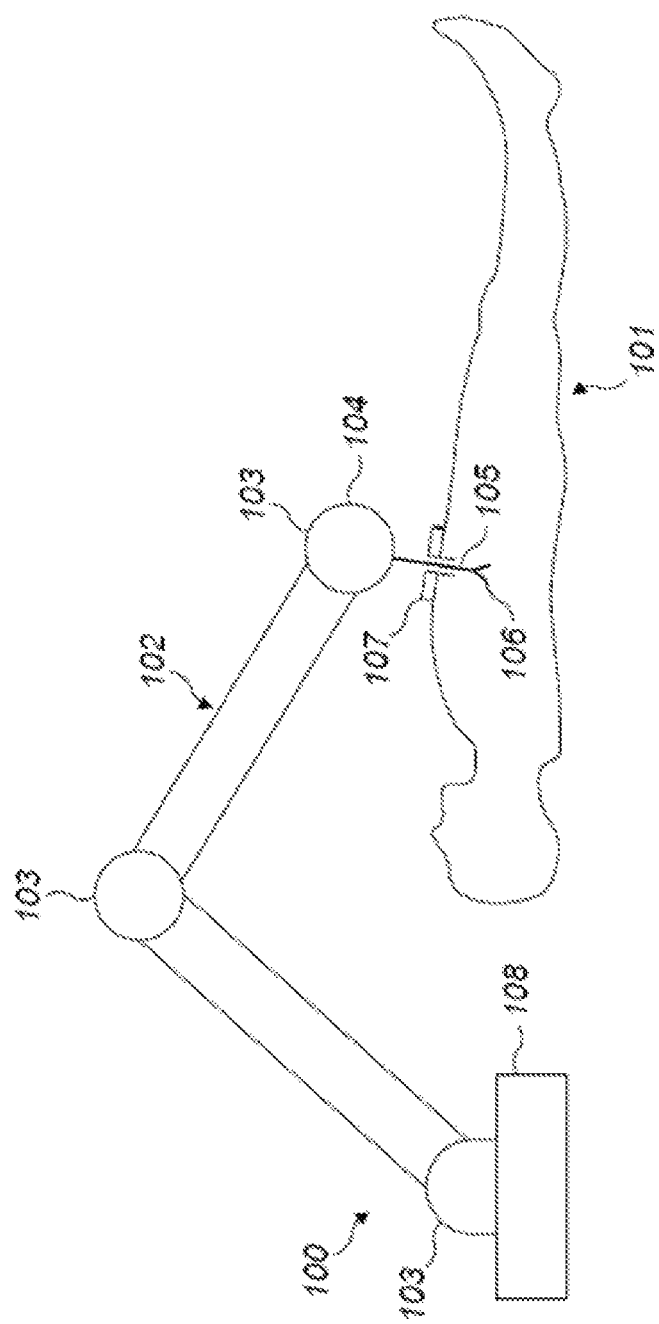
FIG. 1 illustrates a typical surgical robot.

The following description is presented by way of example to enable a person skilled in the art to make and use the invention. The present invention is not limited to the embodiments described herein and various modifications to the disclosed embodiments will be apparent to those skilled in the art. Embodiments are described by way of example only.

A robot arm may be kinematically redundant, or simply 'redundant', in that there are multiple configurations of joints of the arm which result in the same spatial relationship between a base of the arm and an attachment for an instrument at an end of the arm distal from the base of the arm. A redundant arm is able to perform a given task and move (including orient) an instrument or endoscope (attached to the arm) to a desired position with more than one possible arm configuration or "pose".

Such redundancy can give flexibility in the configuration of the arm, but can also lead to problems: some arm configurations may be less desirable than others. This can be because the arm is more likely to collide with another object or a person in the workspace in one configuration than in another configuration. A configuration may be undesirable because it limits subsequent movement, for example of a joint or of the end effector. For example, a particular position of the end effector may be achievable with a given joint well within its operating range, or close to a limit of its operating range. The latter configuration is less desirable in that the given joint may reach its operating limit in a subsequent movement, potentially restricting the movement of the end effector or leading to undesirable high joint speeds at other joints to compensate for the restricted movement. The joint limit acts as a constraint on joint movement, and hence on the arm. Another example of a constraint on arm movement is a contact force applied when a user manually engages with the arm (or a part of the arm) or when a part of the arm collides with its surroundings.

In the present techniques, rather than waiting for a robot arm to reach an undesirable configuration, action can be taken by a control system as the robot arm moves towards that undesirable configuration. Thus, action to avoid the arm ending up in the undesirable configuration can be taken gradually, and need not result in large movements or high accelerations of the arm which may otherwise occur.

One way of doing this, as will be further explained below, is to set a range to one or both sides of a joint angle. The particular joint angle and the size of the range can be selected as desired, for example based on one or more of the characteristics of the arm being used, an instrument to be attached to the arm, the environment of the arm, the procedure that the arm is used to perform, usage data gathered from system telemetry, and one or more algorithms for data analytics. If the joint angle is not within the specified range, then no action need be taken. The control of the arm can proceed in a conventional manner. Once the joint angle crosses the threshold, i.e. the joint angle moves into the specified range, towards a joint angle to be avoided or towards a limit on the rotation of that joint, action can start to be taken. For example, other parts of the arm can be moved so as to move the joint angle away from the joint angle to be avoided. The action taken suitably depends on where within that range the joint angle is. Greater corrective action can be taken where the joint angle is closer to the angle to be avoided. Note that action can be taken where the joint angle is within the specified range, i.e. where the joint angle is static. The present approach can be useful where a static joint angle is determined (such as might occur in a 'snapshot' of the state of the arm), and also where a change in joint angle is determined, for example by comparing a joint angle to a previous joint angle.

In some situations, a combination of joint angles rather than a single joint angle can lead to an undesirable arm configuration. For example, some combinations of joint angles will lead to arm singularities, as will be discussed further below. A singularity can be said to occur where a robot's Jacobian matrix loses rank (i.e. the determinant is zero). This can happen when multiple joint axes become aligned.

The angles of one or more individual joints and the combinations of angles of one or more groups of joints can be considered to represent constraints on the arm configuration. That is, the arm control can be constrained to restrict movement of the arm towards such undesirable configurations. The angles and/or range about the angles, and combinations of angles and/or ranges about the combination of angles can represent constraint criteria constraining movement of the arm.

Techniques described herein can be used to optimise the pose or configuration of a robot arm based on one or more constraint on motion or positioning of the robot arm. Where multiple constraints are present, they may be competing. It may not be possible to completely satisfy all of the constraints at the same time. The relative importance of different constraints can be taken into account in balancing their effect on the arm control, as explained further below. Constraints can be added and/or modified, for example dynamically, i.e. whilst the robot is in operation.

FIG. 1 illustrates a typical surgical robot 100 for use in performing laparoscopic surgery which consists of a base 108, an arm 102, and an instrument 105. The base supports the robot, and is itself attached rigidly to, for example, the operating theatre floor, the operating theatre ceiling, a trolley or a patient bed. The arm extends between the base and the instrument. The arm is articulated by means of multiple flexible joints 103 along its length, which are used to locate the surgical instrument in a desired location (which can include orientation) relative to the patient. The surgical instrument is attached to the distal end 104 of the robot arm. The surgical instrument penetrates the body of the patient 101 at a port 107 so as to access the surgical site. At its distal end, the instrument comprises an end effector 106 for engaging in a medical procedure.

A typical robot arm will comprise a driver for each joint which is configured to drive the joint to move. A typical robot arm will comprise a joint sensor for each joint configured to sense a state of the joint.

The arm must be able to operate whilst the instrument is inside a patient abdomen, as well as during insertion and retraction of the instrument. At these times, the arm is constrained to move in a way which keeps the instrument shaft positioned through a port providing access to the surgical site. Such constraints can reduce the effective number of degrees of freedom of the arm. Constraints on the motion and/or configuration of the arm include avoiding configurations which approach or reach singularities (where the number of degrees of freedom of movement of the robot arm is reduced) or joint limits. Configurations in which the arm contacts or gets close to people or objects in its workspace, such as operating room staff and operating room equipment are also undesirable. Thus, due to these constraints on the movement and/or positioning of the arm, there are some preferred configurations of the arm. The preferred configurations at least partially satisfy a constraint on the arm configuration. A potential collision between multiple arms can also be considered as a constraint. Such a constraint might be 'shared', i.e. it might constrain movement of the multiple arms, or it might be an 'individual' constraint, i.e. it might constrain movement of one arm whilst not constraining movement of another arm. Thus in response to a constraint such as the potential collision between multiple arms, either one arm can be moved or multiple arms can be moved cooperatively.

A constraint can be characterised by a set of constraint criteria, which can comprise a range of values about a given value for a joint state. A joint state can comprise one or more of a joint angle, a joint position, a joint speed or velocity, a joint acceleration and a torque on or about the joint. Taking the example of a joint with a rotation limit of +90°, a range of 10° can be specified within which it can be determined that a constraint condition is met, and an adjustment should be made. In this example, since +90° is a joint limit, the range of angles, a, for which the constraint condition is met is $80° < \alpha \leq 90°$ (or $80° \leq \alpha \times 90°$). At the other end of the operating range of a joint, where the joint limit is −270°, the range would be $-270° \leq \alpha < -260°$ (or $-270° \leq \alpha \leq -260°$).

The constraint can be represented in the control system by a feedback loop. The current state of the joint (here, the joint angle) can be determined and compared to the threshold of the range of joint angles which signify that the constraint condition is met. In the first example in the paragraph above, the threshold is 80°. A difference between the threshold and the current joint angle can be determined. This difference value will increase as the joint angle increases towards the joint limit. The difference value can be used to determine an adjustment to the arm configuration so as to reduce the angle of this joint. The sign of the difference value may indicate a desired direction in which a joint or part of the arm can move to reduce the angle of this joint. The adjustment to the arm configuration can be effected by controlling one or more other joints to move such that the end effector can be positioned or moved as desired whilst reducing (or at least not further increasing) the joint angle of this joint.

The joints of the arm can be controlled via a set of control signals which control the drivers for each of those joints.

Figure 2:
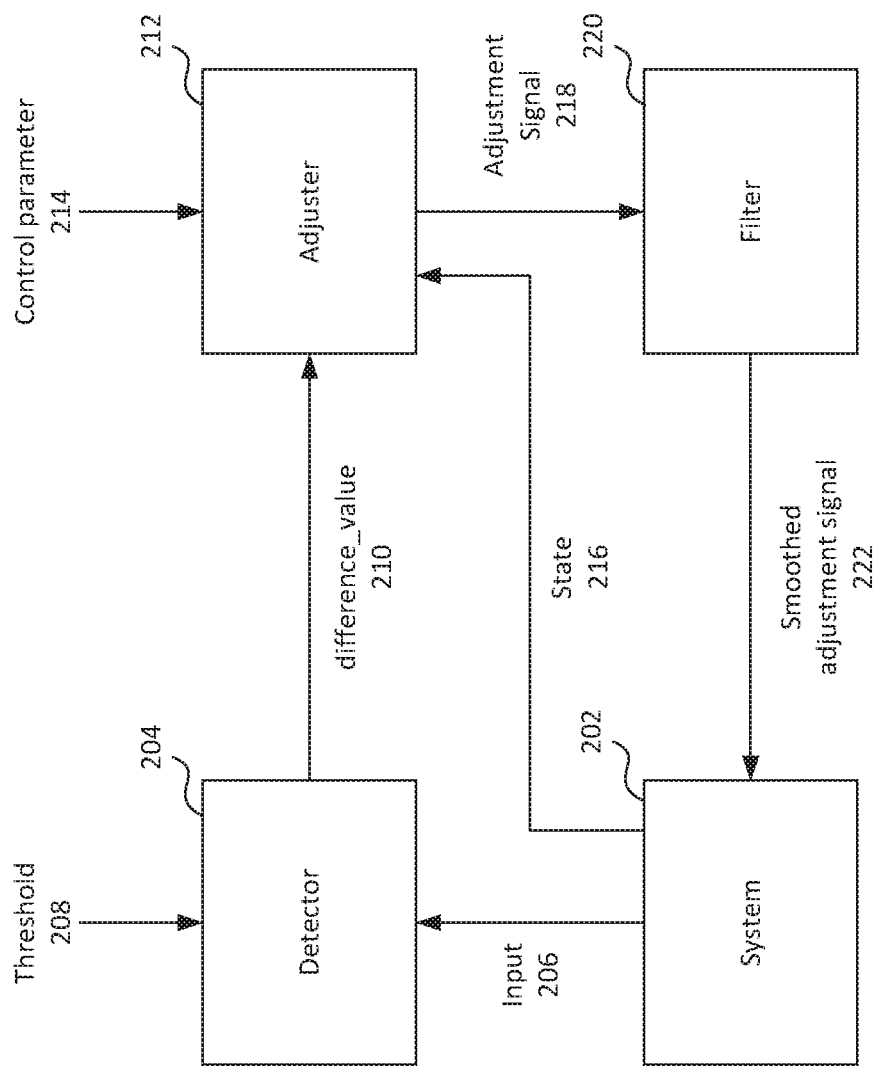
FIG. 2 illustrates a schematic of a control system for a robot arm.

Features of the control system will be described with reference to FIG. 2, which shows a schematic representation of a feedback loop for effecting control of a robot arm. The modules represented in FIG. 2 may be provided in a control unit for controlling a robot arm. The system 202 represents a system to be optimised, i.e. a robot arm. The system represents the physical state of the arm, e.g.

the set of joint angles that defines the configuration of the arm. The set of joint angles may be as expressed through forward kinematics calculations.

A detector 204 is configured to receive an input 206 from the system 202. The input can comprise the state of the arm, including the state of each joint in the arm and/or parameters derived from the arm state. The detector also has access to a threshold value 208. The threshold value 208 represents a threshold to a range of values about a predetermined value for a given joint state value such as a joint angle. For example, the input can comprise a wrist bend angle for a particular joint or angles of a group of joints. The threshold value can be a threshold to one or other or both sides of a predetermined joint bend angle for that particular joint. The detector 204 is configured to determine whether the sensed joint angle (i.e. the joint state value received from the system module 202) is within the specified range. Where the sensed joint state value is within the specified range, the detector can determine that a constraint condition is met.

In the illustrated example, the detector 204 is configured to determine the difference between the sensed joint state value (from the current or any previous iteration) and the threshold value for that joint state. The difference value can be expressed as difference_value=max(0,(joint_state_value−threshold_value))

Thus, where the joint angle is outside the specified range, the difference_value will return a '0', meaning that adjustment of the arm control is not needed. Keeping with the above example, where the joint angle is 70° and the threshold joint angle is 80°, the difference_value will be calculated as difference_value=max(0,(70−80))=0

It is also possible to use matrices as inputs. In this case the maximum value of the matrix elements can be used for further calculations.

Where the joint angle is within the specified range, the difference_value will return a positive value, meaning that adjustment of the arm control should be made. Again, keeping with the above example, where the joint angle is 82°, the difference_value will be calculated as difference_value=max(0(82−80))=2

Other ways of determining the difference_value will be readily apparent, for example where the specified range is a range to either side of a predetermined value for a joint state, or the threshold value is a negative number.

The difference_value 210 is passed to an adjuster module 212. The adjuster 212 determines an adjustment to be made to the configuration of the arm so as to reduce the difference_value, i.e. to move the arm away from the undesirable configuration. The adjustment can take the form of a joint speed for the joint. The adjustment is a positive or negative scalar value, to cause the joint to move in one direction or the other about its axis of rotation. For example, the adjustment can be a signed scalar value representing a joint speed.

The difference_value 210 is a quantitative indication of how close the joint state gets to the predetermined joint state. More generally, the difference_value is a quantitative measure of how close the arm configuration gets to the undesirable configuration. As the difference_value increases, it indicates an increasingly undesirable system state. The adjuster can be configured to determine the adjustment proportional to the calculated difference_value. In this way, as the arm configuration gets closer to an undesirable state, the difference_value increases, and the adjustment increases correspondingly.

The determined adjustment need not be proportional to the difference_value, but could vary non-linearly with the difference_value. For example, the adjustment can increase at a faster rate than the difference_value as the undesirable predetermined joint state is approached. The adjuster can be configured to determine the adjustment algorithmically based on the difference_value. The way in which the adjuster determines the adjustment based on the difference_value may be selected in dependence on one or more of the characteristics of the arm being used, an instrument to be attached to the arm, the environment of the arm, the procedure that the arm is used to perform, usage data gathered from system telemetry, and one or more algorithms for data analytics. Thus, the determination of the adjustment can be suited to the use of the arm.

The adjuster is able to control the effect that the specified constraint has on the system operation. The adjuster 212 can take as an input a control parameter 214. The control parameter can be pre-set or it can be set dynamically during operation of the robot. The control parameter can be set by an operator of the robot system. The control parameter can be one of a set of control parameters accessible to the adjuster. The control parameter can comprise a gain parameter.

In a simple case, the parameter can be set at '1' or '0', and multiplied with the difference_value associated with the constraint. This allows the enabling or disabling of the adjustment based on the constraint.

The control parameter applied by the adjuster can be selected in dependence on one or more of the characteristics of the arm being used, an instrument to be attached to the arm, the environment of the arm, the procedure that the arm is used to perform, usage data gathered from system telemetry, and one or more algorithms for data analytics. For example, different control parameters can be used by the adjuster based on an instrument type attached to the arm, a procedure being performed by the arm, the arrangement of multiple arms in a workspace, and so on.

The adjuster 212 can receive a state signal 216 from the system 202. The state signal suitably represents the state of the robot arm. The adjuster can determine the adjustment in dependence on the state signal. The state signal can indicate whether the arm is static or moving (and in which direction joints of the arm are moving), and whether the end effector is in use or not. The control system can be configured so as not to effect an adjustment of the arm in certain situations such as where the end effector is in use. This can reduce the risk that an inadvertent movement of the arm could affect the operation of the end effector. One way in which the control system can do this is to determine when a particular joint of the arm, such as a wrist joint, is moving, and to only effect adjustment during movement of that joint. One approach to doing this, as is described further elsewhere herein, is to determine a speed of a joint based on successive positions of that joint as indicated by the state of the arm.

The adjuster 212 outputs an adjustment signal 218 based on the adjustment to be made. The adjustment signal can take the form of a signed scalar speed of rotation of a particular joint, or it can take the form of a change in position of a joint. Optionally, the adjustment signal can be passed to the system module 202 via a filter 220. The filter can be a loop filter. The filter suitably filters the adjustment signal to smooth the adjustment signal. Such filtering can make the adjustment movements more acceptable on the mechanics of the arm and/or to an operator of the arm.

The filter 220 outputs the smoothed adjustment signal 222 to the system 202. The system uses the smoothed adjustment signal to determine control signals to effect movement of the joints of the arm. The smoothed adjustment signal can be used to determine a desired movement of a particular joint around the nullspace of that joint. The system uses the smoothed adjustment signal to move the arm towards a more desirable configuration, or at least to restrict movement of the arm towards a less desirable configuration.

Where there are a plurality of constraints, the detector can determine a corresponding plurality of difference_values. For example, the detector can determine a difference_value in respect of each joint for which a predetermined joint state has been set, and also for each group of joints for which predetermined joint states have been set. Thus, the detector can determine a set of values (difference_value$_i$) for i constraints.

The adjuster can be configured to determine an adjustment signal in dependence on multiple difference_values. The adjustment signal can, for example, be a vector comprising vector components each of which represent an adjustment to be made in respect of a constraint and/or in respect of a particular joint. Where different constraints are present, each constraint may result in a different adjustment, i.e. a different scalar value representing a different joint speed. These adjustments may be added together to obtain an overall adjustment. For example the adjustments for a given joint may be added together. The filter may combine different adjustment signals, for example by vector addition. The adjuster can be configured to control the relative importance of each of the constraints or the relative effects that each constraint has on the adjustment signal used to adjust the arm configuration. The adjuster can do this by multiplying each of the difference_values by respective parameters. The control parameter can comprise a set of such respective parameters.

Thus, where multiple constraints are present, the parameters can be used to weight the difference_values associated with each constraint. For example, where a parameter, $\beta_i$, is associated with an ith constraint, the overall difference_value may be determined as $$\text{difference\_value} = \Sigma_i \beta_i \cdot \text{difference\_value}_i$$

where the $\beta_i$ terms sum to 1 (though they need not sum to 1 in all examples).

The calculations of each of the difference_values can occur in parallel. This can reduce any delay in applying the adjustment which might otherwise be introduced into the system control.

Suitably the parameters $\beta_i$ can be adjusted as the system is being used, so as to 'promote' or 'demote' the relative importance of a given constraint during operation of the robot. The control parameter (the set of parameters $\beta_i$) applied by the adjuster can be selected in dependence on one or more of the characteristics of the arm being used, an instrument to be attached to the arm, the environment of the arm, the procedure that the arm is used to perform, usage data gathered from system telemetry, and one or more algorithms for data analytics. Thus the system can enable automatic adjustment of various competing constraints. This can be done as the arm is being used. For example, different control parameters can be used by the adjuster based on an instrument type attached to the arm, a procedure being performed by the arm, the arrangement of multiple arms in a workspace, and so on.

The vector components of the adjustment signal vector can be added to one another to form an overall adjustment signal. It will be understood that different constraints may cause an adjustment to the same joint, and that such adjustments may be opposite to one another. I.e. one constraint may cause the control system to try and adjust a joint by a positive angle, and another constraint may cause the control system to try and adjust that joint by a negative angle. These constraints will thus be seen to be competing with one another. In a simple addition, the constraint causing the greater adjustment of this joint will 'win', i.e. the joint will tend to move in the direction of the greater adjustment. To address this, the control parameter can be used to affect the relative importance of each constraint. Thus, a more important constraint which would cause a relatively smaller joint rotation can still dominate over a less important constraint which would cause a relatively larger joint rotation. In this way, the behaviour of the arm can be controlled as desired. The control parameter (or in the case of multiple constraints, the set of separate parameters) can be used to ensure that the arm behaves as expected, or as required, in different situations. This can be of especial importance in a surgical setting, where a surgical robot arm needs to behave with a high degree of certainty, for safety and regulatory reasons, amongst others.

Figure 3:
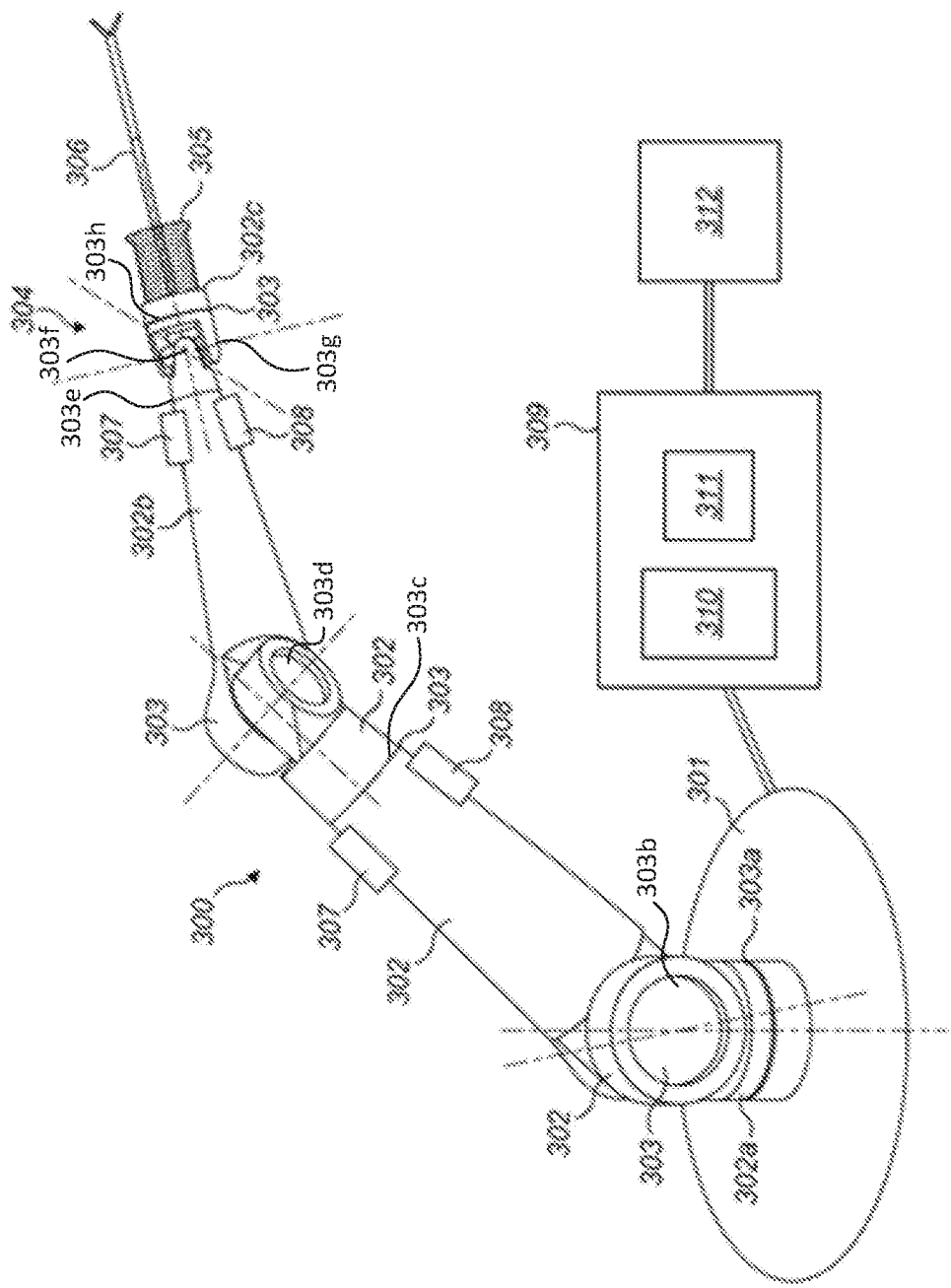
FIG. 3 illustrates another surgical robot.

The present techniques will now be described further with respect to a particular arrangement of a robot arm. FIG. 3 illustrates a surgical robot having an arm 300 which extends from a base 301. The arm comprises a number of rigid limbs 302. The limbs are coupled by revolute joints 303. The most proximal limb 302a is coupled to the base by a proximal joint 303a. It and the other limbs are coupled in series by further ones of the joints 303. Suitably, a wrist 304 is made up of four individual revolute joints. The wrist 304 couples one limb (302b) to the most distal limb (302c) of the arm. The most distal limb 302c carries an attachment 305 for a surgical instrument 306. Each joint 303 of the arm has one or more motors 307 which can be operated to cause rotational motion at the respective joint, and one or more position and/or torque sensors 308 which provide information regarding the current configuration and/or load at that joint. Suitably, the motors are arranged proximally of the joints whose motion they drive, so as to improve weight distribution. For clarity, only some of the motors and sensors are shown in FIG. 3. The arm may be generally as described in our co-pending patent application PCT/GB2014/053523.

Controllers for the motors, torque sensors and encoders are distributed within the robot arm. The controllers are connected via a communication bus to a control unit 309. The control unit 309 comprises a processor 310 and a memory 311. The memory 311 stores in a non-transient way software that is executable by the processor to control the operation of the motors 307 to cause the arm 300 to operate in the manner described herein. In particular, the software can control the processor 310 to cause the motors (for example via distributed controllers) to drive in dependence on inputs from the sensors 308 and from a surgeon command interface 312. The control unit 309 is coupled to the motors 307 for driving them in accordance with outputs generated by execution of the software. The control unit 309 is coupled to the sensors 308 for receiving sensed input from the sensors, and to the command interface 312 for receiving input from it. The respective couplings may, for example, each be electrical or optical cables, and/or may be provided by a wireless connection. The command interface 312 comprises one or more input devices whereby a user can request motion of the end effector in a desired way. The input devices could, for example, be manually operable mechanical input devices such as control handles or joysticks, or contactless input devices such as optical gesture sensors. The software stored in the memory 311 is configured to respond to those inputs and cause the joints of the arm and instrument to move accordingly, in compliance with a pre-determined control strategy. The control strategy may include safety features which moderate the motion of the arm and instrument in response to command inputs. Thus, in summary, a surgeon at the command interface 312 can control the instrument 306 to move in such a way as to perform a desired surgical procedure. The control unit 309 and/or the command interface 312 may be remote from the arm 300.

The illustrated surgical robot comprises a single robot arm. Other surgical robot systems may comprise a plurality of surgical robots and/or a plurality of robot arms. For example, other example surgical robot systems may comprise a surgical robot with a plurality of robot arms that can each receive and manipulate a surgical instrument, or they may comprise a plurality of surgical robots that each have a robot arm that can receive and manipulate a surgical instrument.

For ease of reference, the joints of the arm illustrated in FIG. 3 can be labelled as J1 (303a), J2 (303b), J3 (303c), J4 (303d), J5 (303e), J6 (303f), J7 (303g) and J8 (303h). Joint J4 can be considered as an "elbow" of the illustrated arm. The kinematics of this arm arrangement permit the elbow joint to move within a known and variable "nullspace" whilst keeping the wrist of the arm (joint J6/J7 in the illustrated example), which couples to the attachment for the instrument, at a desired position, as commanded by the command interface. Constraints applied to adjust movement and/or position of the arm can help ensure that the elbow is in the optimum location within that nullspace in order to perform any given task within a user-specified operating mode.

Figure 4:
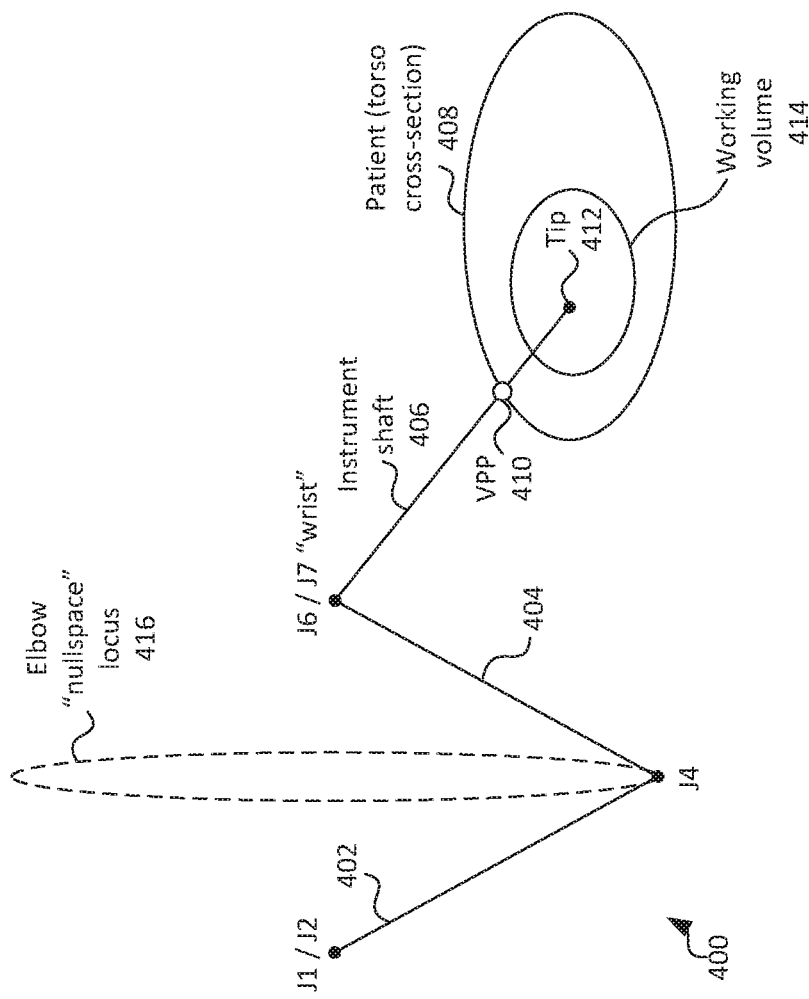
FIG. 4 illustrates a schematic of a robot arm showing an elbow nullspace.

A schematic of the arm is illustrated in FIG. 4, showing the nullspace locus of the J4 joint of the arm illustrated in FIG. 3. The arm is generally indicated at 400. The representation of the arm has been simplified in this figure. As illustrated, the arm comprises a first section 402 extending between the first two joints (J1/J2, the base of the arm) and the fourth joint (J4, the arm elbow). The arm comprises a second section 404 extending between the fourth joint (J4) and the sixth and seventh joints (J6/J7, the arm wrist). The instrument 406 extends distally of the wrist and penetrates a patient torso 408. The instrument shaft penetrates the patient torso through a port at a virtual pivot point (VPP) 410. The virtual pivot point can be defined as a distance along the instrument shaft from the end of the robot arm about which the instrument can be pivoted. The tip of the instrument 412 extends into a working volume 414. The locus of the elbow (J4) nullspace is schematically shown in dashed lines 416. Joints J3, J5 and J8 are not explicitly shown here. Movement of the elbow along its locus of movement can be enabled by coordinated movement of all of the joints.

In this setup of the arm, multiple constraints can usefully be applied. Some examples of such constraints are given herein. It will be understood that other constraints may be applied instead of or in conjunction with any one or more of the examples here. Two of the example constraints described here are applied to the movement of the pivotal joint J2 to restrict movement of that joint towards some angular positions, but such constraints might usefully be applied to any other joint or combination of joints of the arm.

Wrist Bend

A large wrist-bend angle, i.e. a large angle between the J5-J6/J7 link, and J6/J7-VPP-tip vectors, is generally undesirable because this can severely restrict the trade-off that can be made between J6 and J7 joint angles using J5. As the wrist-bend angle increases beyond 90°, the wrist bend is sustained chiefly by J7 (with J6 having a very limited range). A simple way to reduce the wrist-bend angle is to move the elbow (J4) in the direction which reduces this angle. A good solution is when J4 is as close as possible to the projected instrument axis vector: in this position all the joints line up in a plane and wrist bend is globally minimised.

The threshold at which a constraint condition can be determined to exist can be set at 90°. Thus when the wrist-bend angle exceeds 90° the control system can determine a positive difference_value, which can be used to effect adjustment of the arm configuration. The corresponding adjustment signal can be modified by a wrist bend control parameter, which can represent a gain applied to the value of the difference between the wrist-bend angle and the threshold. This difference can be considered to represent an 'error' in the wrist-bend angle which is to be reduced.

Barrel Singularity

A "barrel" singularity can be deemed to occur when the wrist lines up with the projected axis of J2. The effect of such a singularity is to prevent J2 from being able to move the wrist spatially. Instead, rotation of the J2 joint will rotate the wrist about the J2 axis. In this position, there are strictly only two degrees of freedom. The situation is analogous to polar coordinates in that J1 (or J3) can "rotate" the wrist and J4 can move the wrist in and out radially. Movement in the z-direction is restricted. Here, the z-direction is taken with reference to the arm base reference frame, and can be considered to be an 'upwards' direction, where the arm base is mounted on the floor.

A FAIL condition can be raised if the wrist comes too close to the barrel singularity. This can be assessed based on a wrist to J2 axis distance (e.g. the shortest distance between the wrist and the J2 axis). It is also possible to try to move the elbow (J4) to move the wrist away from the J2 axis if the wrist comes within a virtual cylinder defined about the J2 axis.

The specified joint angles in this example are those that cause the wrist to line up with the J2 axis. The thresholds to the range about these specified joint angles can define the limits of the cylinder 'exclusion zone' defined about the J2 axis. Conceptually, the thresholds can define the radius of the cylinder.

Thus when the wrist moves into the virtually defined cylinder, the control system will determine a positive difference_value, which can then be used to effect adjustment of the arm. The adjustment signal can be modified by a barrel control parameter, which can represent a gain applied to a value quantifying how far within the cylinder the wrist penetrates, i.e. how far past the threshold the wrist has gone. This value can be considered to represent an 'error' in the joint angles of that arm configuration which is to be reduced.

It is also possible to define a volume within the cylinder, which is to be treated as a hard boundary for movement of the wrist. For example, a smaller cylinder can be defined about the projected J2 axis. This can be considered as a 'no-go' zone for the wrist. Where the arm configuration causes the wrist to reach (or cross) the boundary of this smaller cylinder, a FAIL condition can be raised. The FAIL condition can restrict or prevent further movement of the arm that violates this constraint. It may still be possible to move the arm so as to remove the wrist from within the boundary of this smaller ('no-go') cylinder. Alternatively, the FAIL condition may require intervention from an operator for the procedure to be able to continue.

In general, defining multiple boundaries, as in the barrel singularity example here, may be useful for changing one or more criteria. This can be achieved by modifying a weighting function where a further boundary is crossed. This approach is not restricted to singularities, but can be useful in response to a variety of constraints, e.g. a single joint angle: one weighting function can be used where a first threshold is crossed (e.g. 15° from a joint limit) and another weighting function can be used where a second threshold is crossed (e.g. 5° from a joint limit).

J2 Angle Too Small

When J2=0° (i.e. when the arm segment extending between the J1/J2 joints and the J4 joint is vertical) difficulties in moving the arm can arise.

When J2=0°, the wrist and elbow Jacobian matrices have near-zero valued singular values (after a Singular Value Decomposition). This can affect the relationship between the Cartesian position demanded by a command interface and the changes required to joint angles to effect the position change. A worst-case relationship between the demanded Cartesian position and the joint angle changes is determined by the reciprocal of the singular values. Thus near-zero singular values will give rise to undesirably high joint speeds for small movements.

The physical effect of this is that the system operator has to "twist" the J3-J4 link to get it to move compliantly, rather than a force being applied along the elbow axis.

Another undesirable effect occurs when J2=0° and J3=90°: there are just 2 degrees of freedom for the wrist so that it cannot be moved in 3 dimensions very easily.

The threshold at which a constraint condition can be determined to exist can be set at a J2 joint angle value that is a small (positive or negative) value, for example ±5°. Thus the range of J2 joint angles at which a constraint condition can be determined to exist is 10°; this range is centred about 0°. When the J2 joint angle enters this range, the control system can determine a difference_value which can be used to effect adjustment of the arm configuration. The adjustment signal can be modified by a 'J2 small control parameter', which can represent a gain applied to a value quantifying how far within the specified range the J2 joint angle goes. This value can be considered to represent an 'error' in the J2 joint angle which is to be reduced.

J2 Angle Too Large

In the arm arrangement illustrated in FIG. 3, the range of J2 is −90° to +135°. It is preferable to restrict the J2 joint from rotating so as to get too close to the limits. This is because approaching the limits can reduce the ability of the arm to accommodate subsequent movements. Wrist bend minimisation can potentially force joint J2 towards its limits of rotation if the elbow (J4) locus goes outside a range that can be supported by rotation about J2.

The occurrence of this potential problem can be reduced by introducing a corrective, opposing force. A simple form is to define a threshold spaced from the limits which, if crossed, causes a corrective elbow movement. The corrective elbow movement can be proportional to a value quantifying how far past the threshold the J2 joint angle goes.

The thresholds at which a constraint condition can be determined to exist can be set at J2=−75° and J2=+120° (i.e. the specified ranges of J2 joint angles at which a constraint condition can be determined are:

$$-90° \leq J2\_angle \leq -75° \text{ (or } -90° \leq J2\_angle < -75°) \text{ and} \quad (i)$$

$$120° \leq J2\_angle \leq 135° \text{ (or } 120° \leq J2\_angle < 135°). \quad (ii)$$

In this example the range of angles is the same at both limits of the J2 joint angles, though this need not be the case. One of the ranges can be smaller than the other. Other values for the range(s) of angles can be used.

When the J2 joint angle is, for example, either (i) less than −75° or (ii) greater than 120° the control system can determine a difference_value, which can be used to effect adjustment of the arm configuration. The corresponding adjustment signal can be modified by a 'J2 control parameter', which can represent a gain applied to the value of the difference between the J2 joint angle and the relevant threshold. This difference can be considered to represent an 'error' in the J2 joint angle which is to be reduced.

Note that in the second example above ("J2 angle too small"), the case where J2=0° is undesirable. However, it should remain possible for the J2 joint to rotate through this angle during operation of the robot. This is an example of where a constraint is not to be treated as a 'hard' constraint, in that it should be possible for J2 to equal 0°. However, once other constraints have been at least partially satisfied, the arm may be desired to be moved away from the configuration in which J2 does equal 0°. The selection of which constraint(s) are satisfied before other constraint(s) can be controlled through use of an appropriate control parameter, as discussed elsewhere herein.

During operation of the robot, the adjustment signal may attempt to move the arm in a different way to that resulting from an operator command input to the system such as a desired movement of the end effector. It is desirable for the operator's commands to have a higher priority on arm movement. The integration of the arm adjustment commands with operator-derived wrist movement commands will now be described.

The adjustment signal determined by the control system described herein can be modified with a 'soft' gating gain which can be derived from a speed associated with the arm. Suitably the gating gain is derived from the speed of the wrist of the arm—this can be termed a wrist speed gain. Use of such gating can help coordinate movement between joints of the arm, such as the elbow and wrist joints. The gating can be used to grant wrist movement, commanded by an operator's controls, a higher priority than elbow movement. The adjustment signal can be multiplied with this wrist speed gain.

Following the multiplication of the adjustment signal with the wrist speed gain, the result can be filtered so as to restrict jerky elbow movements. This multiplication product can then be superposed on a compliance-induced elbow force resulting in a "synthetic force", which is fed into the elbow nullspace inverse kinematics algorithm to cause updates to joint positions by small increments. The arm configuration changes caused by the "synthetic force" may be arranged to keep the wrist still. For example, the "synthetic force" may be arranged so as not to affect end effector movements commanded by an operator controlling the arm.

Figure 5:
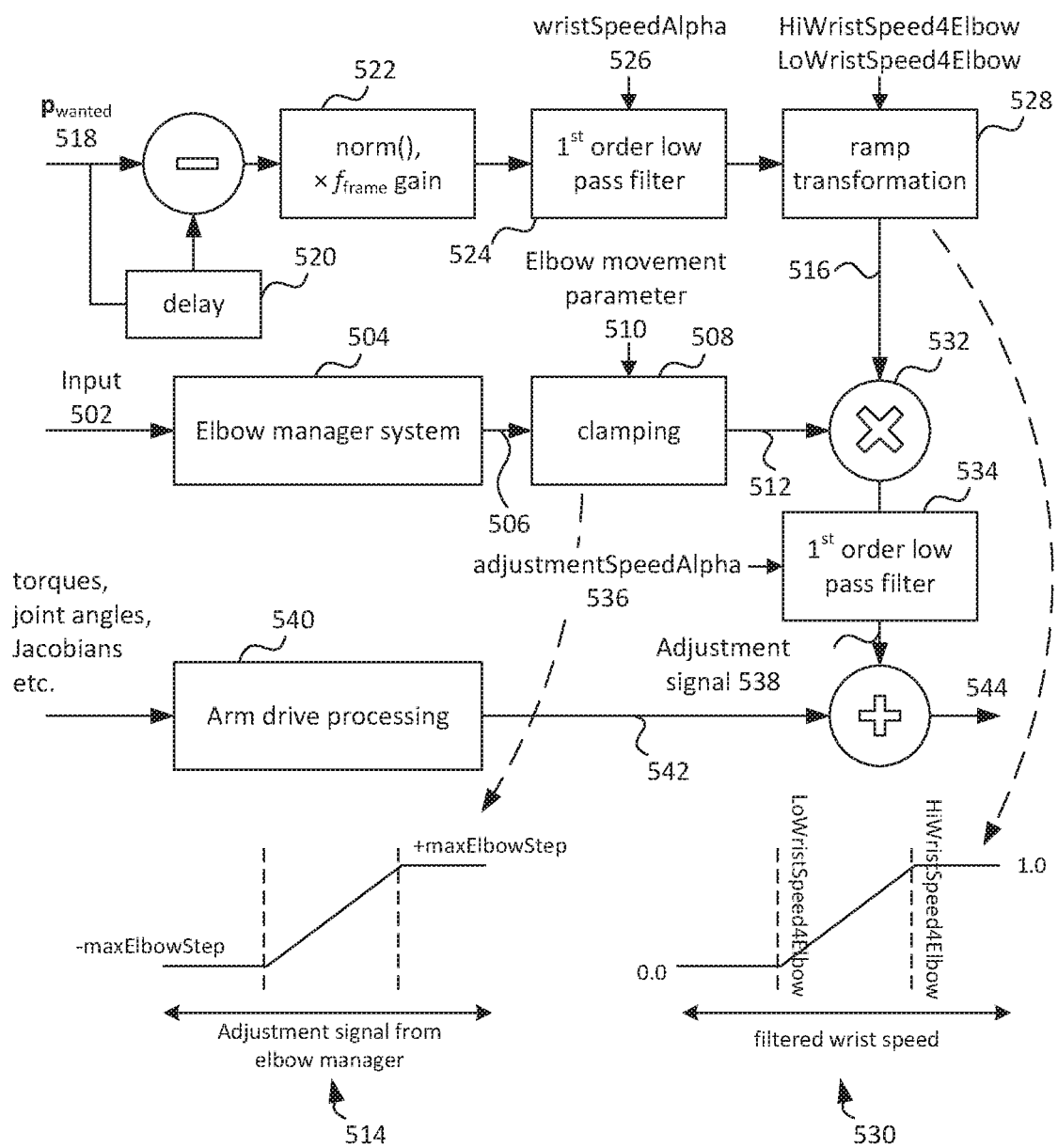
FIG. 5 illustrates a state diagram of a method for implementing a control system relating to control of the elbow joint.

This process is highlighted in FIG. 5, illustrating a state diagram of a method for implementing a control system relating to control of the elbow joint (though, as discussed elsewhere herein, control of other joints and/or combinations of joints can be effected using the described techniques). Input parameters 502 relating to the state of the robot arm and the thresholds corresponding to one or more constraint conditions are received by an elbow manager 504. The elbow manager can generally correspond to the detector 204 and adjuster 212 modules illustrated in FIG. 2. The elbow manager is configured to output an adjustment signal 506 for controlling adjustment of the elbow in response to a constraint.

The adjustment signal 506 is fed to a clamping module 508 which ensures that the movement commands generated in response to the adjustment signal do not exceed a maximum elbow movement step size. The maximum step size can be pre-set or it can be set dynamically. As illustrated, the clamping module receives an elbow movement parameter 510 which comprises the maximum elbow movement step size (maxElbowStep). Where the adjustment signal indicates that the elbow should be moved by an amount that does not exceed ±maxElbowStep, the adjustment signal is passed to an output 512 of the clamping module. Where the adjustment signal indicates that the elbow should be moved by an amount that exceeds the positive (or negative) maxElbowStep, then the adjustment signal is modified so as to limit the adjustment to the positive (or negative) maxElbowStep, i.e. the adjustment to the elbow position is clamped at the respective maxElbowStep limit. This clamping is schematically illustrated at 514. This avoids the system from attempting to effect undesirably large movements which can lead to high joint speeds.

The output 512 therefore represents the adjustment signal or a clamped version of the adjustment signal. This signal is passed to a multiplier, which multiplies the signal with a gating gain 516 derived from the wrist speed. There are different ways that the wrist speed can be determined, including obtaining a measure of the wrist speed from the kinematics of the robot control system. The approach illustrated in FIG. 5 enables an estimation of the wrist speed to be obtained quickly and easily, at relatively low processing power. In practice, this estimation is likely to be good enough for use as the gating gain. In situations where a more accurate speed is needed, then the wrist speed can be obtained in a different manner.

Estimation of the wrist speed is obtained based on filtering the Euclidean distance of wrist movements. This is achieved by comparing the commanded position 518, $p_{wanted}$, at successive frames. This is done by passing the commanded position through a delay module 520 to introduce a one frame delay, then subtracting the delayed position from the position of the succeeding frame. The result of this subtraction (the change in position, in metres, between successive frames) is scaled by the frame rate in Hz, $f_{frame}$, 522 (to obtain a wrist speed in metres/second). This provides an instantaneous wrist speed, but this might be noisy. The wrist speed is then filtered to reduce the noise, for example with a first-order low-pass filter 524. The filter 524 takes as an input a coefficient wristSpeedAlpha 526 which is determined from the desired filter time constant $T_1$ (seconds) and $f_{frame}$. A default value of $T_1$=0.1 s is used, but this can be varied as desired. The filter coefficient is defined as $$wristSpeedAlpha = e^{\left(-\frac{1}{f_{frame}T_1}\right)}$$

Mathematically, the filtering of the wrist speeds can be $y(j)=y(j-1)*(wristSpeedAlpha)+x(j)*(1-wristSpeedAlpha)$ where y( ) is the filtered wrist speed, x( ) is the unfiltered wrist speed, j indicates the current frame and (j−1) indicates the previous frame.

The filtered wrist speed is then passed to a ramp transformation module 528 which effects a 'soft gating' of the filtered wrist speed. The ramp transformation module takes as inputs two parameters: LoWristSpeed4Elbow (which determines where the soft gating reaches a gain of zero) and HiWristSpeed4Elbow (which determines where the soft gating reaches a gain of 1). The ramp transformation module thus enables control of the gating as a function of wrist speed.

Mathematically, the ramp transformation can be
if ws < LoWristSpeed4Elbow
ramp_transform ( ws ) = 0

```
if LoWristSpeed4Elbow ≤ ws ≤ HiWristSpeed4Elbow
    ramp_transform ( ws ) =   ( ws − LoWristSpeed4Elbow ) /
                              ( HiWristSpeed4Elbow − LoWristSpeed4Elbow )
if HiWristSpeed4Elbow < ws
    ramp_transform (ws) = 1
where ws is the filtered wrist speed.
```

Default values for the parameters are LoWristSpeed4Elbow=0.01 m/s and HiWristSpeed4Elbow=0.3 m/s. I.e. when the wrist speed drops to 0.01 m/s or below, a gating gain 516 of zero is applied to the adjustment signal 512, meaning that adjustment of the elbow is not applied. This ensures that when the wrist stops the elbow is also stopped. When the wrist speed reaches or exceeds 0.3 m/s, a gating gain 516 of 1 is applied to the adjustment signal 512, meaning that the full adjustment output by the clamping module 508 is applied. At wrist speeds between these values, a gain of between 1 and zero can be applied. As illustrated at 530 the gain linearly increases between zero and 1, though other variations of the gain value are possible.

The gating gain 516 is multiplied with the (clamped) adjustment signal 512 at 532 and the result passed to a further filter such as a first-order low-pass filter 534. This filter acts as a loop filter to filter the adjustment signal to prevent undesirably jerky elbow movements. It can be considered to be equivalent to a mass and damper impedance model (a first order infinite impulse response filter in the velocity domain), but it is sensible to parameterise the filter in terms of a time constant $T_2$ (with a default value of $T_2$=0.1 s). The filter 534 takes as an input a coefficient adjustmentSpeedAlpha 536 which is determined from the desired filter time constant $T_2$ (seconds) and $f_{frame}$. A default value of $T_2$=0.1 s is used, but this can be varied as desired. The filter coefficient is defined as $$adjustmentSpeedAlpha = e^{\left(-\frac{1}{f_{frame}T_2}\right)}$$

The adjustment signal 538 output from the filter 534 is combined with an output from an arm drive processing system 540. The arm drive processing 540 can take as inputs torques at or about one or more joints, a joint angle of one or more joints, a Jacobian of the robot arm, and so on. The output from the arm drive processing represents a 'physical' adjustment signal 542 for effecting control of the arm in response to compliance-based inputs. Such compliance-based inputs can include operator-derived inputs, where an operator can physically interact with the robot arm to effect driven movement of the arm. For example, an operator can push on a part of the arm; the arm senses the force with which the operator pushes on the arm, and in response drives motors of the arm to effect movement on that part of the arm in the direction in which the operator is pushing the arm. Compliance-based inputs can also include inputs relating to the weight of the arm (e.g. torque at or about one or more joints), vibrations affecting the arm, patient movement, and so on. The arm drive processing 540 suitably comprises elbow compliance processing.

The adjustment signal 538 is added to the physical adjustment signal 542 to generate a 'total adjustment signal' 544. The total adjustment signal is passed to an inverse kinematics algorithm (which may be provided in the same module or processor, or at a separate module or processor) which is configured to determine drive signals for controlling the robot arm. For example, the total adjustment signal is passed to an inverse kinematics nullspace algorithm. In this way, the elbow manager-derived movements can be superposed with compliance-induced movements and used in determining robot drive signals. A likely effect of the superposition is that elbow manager-derived movements may dominate over compliance-induced movements during active wrist movement, such as in a surgical mode, and that compliance-induced movements may dominate over elbow-manager-derived movements when the wrist is not moving.

Different values for one or both of $T_1$ and $T_2$ and/or the gain values can be selected in dependence on one or more of the characteristics of the arm, an instrument to be attached to the arm, the arm environment, the procedure the arm is used to perform, usage data gathered from system telemetry, and one or more algorithms for data analytics. This enables the behaviour of the robot arm to be controlled more precisely, according to a given situation in which the arm is to be used.

The filters described above could be any suitable type of linear low-pass filter. Wrist speed filtering, whilst desirable in the above implementation, is optional, for example where the speed is determined in an alternative manner so that it is less likely to comprise noise.

The predetermined values and/or the specified ranges about those predetermined values which define one or more constraints can be modified. For example they can be modified in dependence on one or more of the characteristics of the arm, an instrument to be attached to the arm, the arm environment, the procedure the arm is used to perform, usage data gathered from system telemetry, and one or more algorithms for data analytics. This permits a more refined control over the arm and the way in which the constraint conditions cause adjustment of the arm.

In the above discussion of the elbow manager, the adjustment signal is a scalar value because the elbow is constrained to trace a circle delimited by its nullspace. The arm state is needed to determine the direction that the elbow must move to minimise the error (based on the normalised nullspace vector, $\theta_{null}$, which moves the arm in the direction in which the elbow axis points). In other examples, where the nullspace has two or more dimensions, a different vector-value parameterization can be employed.

The constraints on arm movement and/or positioning can be assessed quantitatively. Thus, the way in which each constraint or combination of constraints affects the arm control can be analysed. Such analysis can inform the way in which the arm is used in a procedure, for example so as to reduce the likelihood that the arm will move towards a relatively less desirable configuration in the procedure. Such analysis can also inform the modification of constraint values.

The techniques herein enable constraints to be added, modified and removed easily. Constraints can also be combined easily. Since the behaviour of each constraint can be characterised by one or more parameter independent of those relating to other constraints, such addition, modification or deletion of constraints can be done without needing to alter the parameters (behaviour) of other constraints. Suitably the constraints and their respective parameters can be viewed and modified via an API.

Further, each constraint is able to be tested individually. Such testing may be done 'offline', i.e. without requiring a procedure to be physically performed by the arm. This is particularly desirable in the field of medical robotics where it is useful to be able to predict and/or validate outcomes of surgeon control of a surgical robotic arm and to ensure that the system is deterministic.

The elbow manager is conveniently able to combine multiple constraints into a single output which can be compared to a threshold, such as the threshold represented as maxElbowStep in FIG. 5. This can be used as part of telemetry data to learn about system performance, enabling optimisation of constraints offline.

Figure 6:
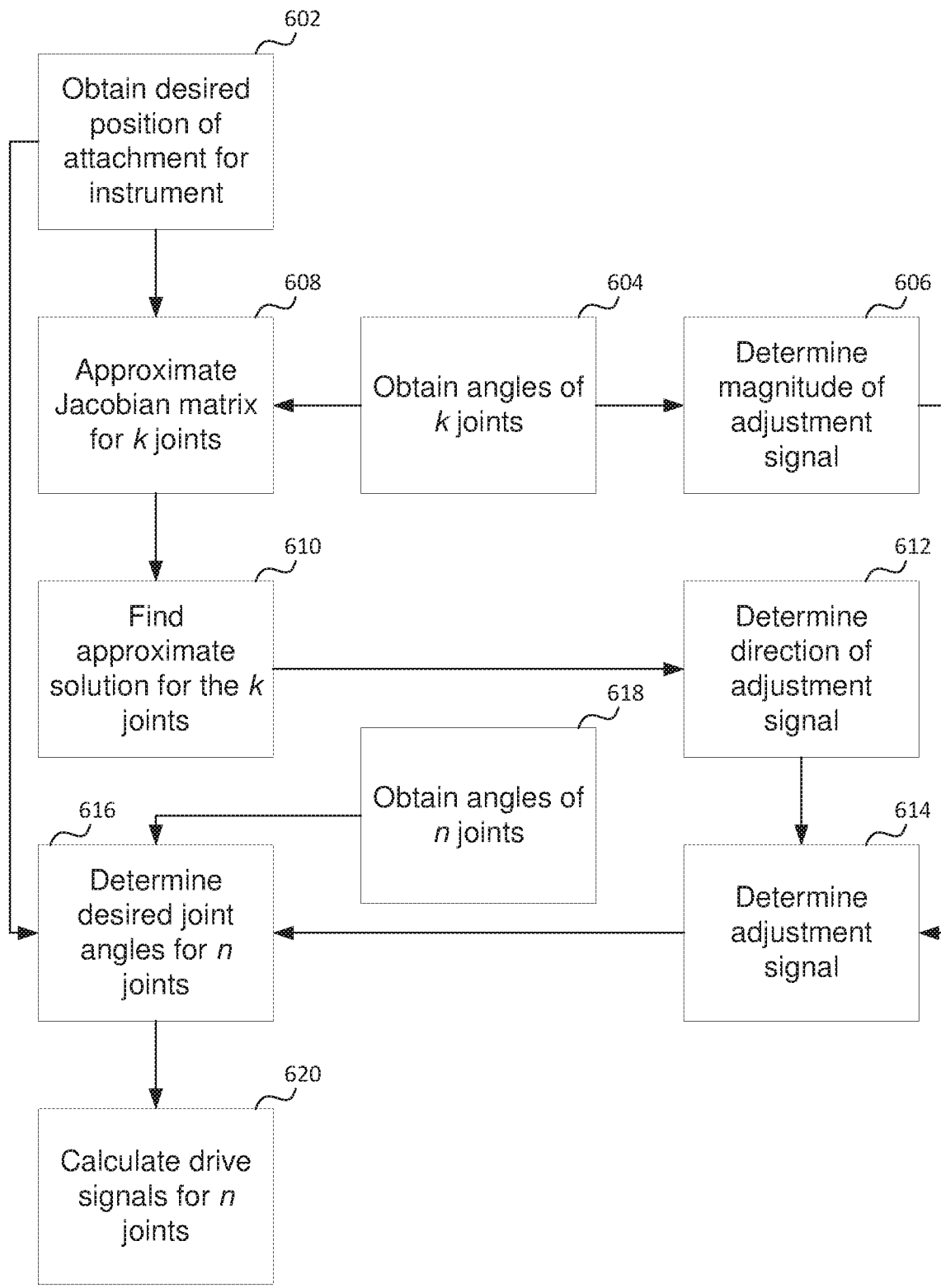
FIG. 6 illustrates a method of controlling a robotic system.

A method of controlling a robotic system will now be described with reference to FIG. 6. A desired position of a portion of the robot arm is obtained (602). Here the position of the attachment for the instrument is obtained, but this could also be a position of a wrist. It will be understood that the position of the attachment for the instrument can be determined from (e.g.) the wrist position and vice versa. The desired position can be obtained from a position commanded by an input device at a surgeon console. In the below, positions of the attachment for the instrument will be discussed but it is to be understood that positions of other parts of the arm could be used in other examples.

The robot arm comprises n joints. Angles of k joints are obtained (where k<n) (604). More generally, the state of the k joints can be obtained. Suitably the k joints are the k most proximal joints of the arm, i.e. J1-Jk. In an implementation of the elbow manager discussed above, k=4 and so the angles for J1-J4 are obtained. The joint angles can be represented as a vector, for example, where k=4

$$q=[q_1,q_2,q_3,q_4]$$

If required, zeros can be appended to q in respect of the remaining joints. So, where there are 8 joints (J1-J8), q can be written as $$q=[q_1,q_2,q_3,q_4,0,0,0,0]$$

It is convenient to obtain from the arm or from an arm control system angles of all n joints at once. These angles can conveniently be stored locally. The angles of the k joints may then be accessed.

The k joint angles are used, for example as described above, to determine a magnitude of an adjustment signal (606). This can take account of a single constraint criterion or multiple, possibly competing, constraint criteria. The k joint angles are also used, together with the desired position of the attachment for the instrument, to generate an approximation of the Jacobian matrix for the k joints (608) and find an approximate solution for the k joints (610). The generation of the approximation of the Jacobian can comprise an iterative process. A small number of iterations has been found to provide a good enough solution here—as described, the solution is used to determine the direction of the adjustment signal. This solution is not used generate drive signals for controlling the arm. 2 or 3 iterations has been found to be sufficient.

A first approximation can be determined. Using the approximated Jacobian and taking the distance between the current position of the attachment for the instrument and the desired position of the attachment for the instrument as a position error, a least-squares method is used to find the minimum norm solution for J1-Jk that lies within the nullspace with respect to joint Jk. As an example, where k=4 (i.e. the joint is the elbow joint), the nullspace (the elbow nullspace) can be defined as a 4×1 vector, θnull that satisfies the formula $(Jwrist)^T \cdot (\theta null)=0$ (this is zero for a stationary wrist). The instantaneous direction in Cartesian coordinates along the nullspace can be given by the normalised form of $(Jelbow)^T \cdot (\theta null)=dXYZElbow$.

A more robust version can use the Levenberg-Marquardt (LM) algorithm (a damped least-squares (DLS) method). In general, a method is used to solve the under-constrained equation, $\dot{x}=J\dot{q}$. A good solution is given by the least-squares inverse in the sense that it minimises the residual norm $\|J\dot{q}-\dot{x}\|$. To avoid the need for a pseudoinverse, diagonal loading is used before inversion. The diagonal loading can be achieved by the identity matrix weighted by a small value, $\lambda$. The parameter $\lambda$ is adjusted to minimise a cost function. An example of the cost function is the Euclidean distance to the desired position of the attachment for the instrument: norm ($p_{error}$). The parameter $\lambda$ can be made bigger (e.g. ten times bigger) or smaller (e.g. ten times smaller) depending on the value of the cost function. Pseudocode for implementing this example approach is presented below.

- Initialise $J_{attachment\_for\_instrument}$, $p_{error}$, $\theta$. Set tol = 1e-6 (1μm), $\lambda$ = 1e-8
- for N iterations:
  - Solve Normal Equations with ($J_{attachment\_for\_instrument}$, $p_{error}$, $\theta$) (with LM modification) to get $\Delta\theta$
  - $\theta_{trial} = \theta + \Delta\theta$
  - Obtain $J_{attachment\_for\_instrument\_trial}$, $p_{trial}$ via Forward Kinematics from $\theta_{trial}$
  - $p_{error\_trial} = p_{trial} - p_{wrist}$
  - if norm($p_{error\_trial}$) < norm($p_{error}$)
    - # ACCEPT!
    - $\theta = \theta_{trial}$
    - $p_{error} = p_{error\_trial}$
    - $\lambda = \lambda \times c_{smaller}$
  - else
    - # REJECT
    - $\lambda = \lambda \times c_{bigger}$
  - if norm($p_{error}$) <= tol
    - # Stop. Report SUCCESS.
- If norm($p_{error}$) > tol
  - # Stop. Report FAIL.

The approximate solution for the k joints can comprise a set of joint velocities. The approximate solution can comprise a joint velocity per joint of the k joints. The approximate solution for the k joints can indicate a position in space towards which the kth joint is to move. The approximate solution is used to determine a direction of the adjustment signal (612). The direction of the adjustment signal is preferably tangential to a boundary of the nullspace of the kth joint. The magnitude and direction of the adjustment signal are used to determine the adjustment signal (614).

The desired position of the attachment for the instrument (602) and the determined adjustment signal (614) are provided to a module for determining desired joint angles for all n joints (616). Angles (i.e. current angles) of the n joints are obtained (618). More generally, the state of the n joints can be obtained. As mentioned above, it is convenient to obtain from the arm or from an arm control system angles of all n joints at once. These angles can conveniently be stored locally. The angles of the n joints may then be accessed. That is, the method steps of obtaining angles of k joints and of obtaining angles of n joints need not comprise separate measurement steps, though they might in some examples. Preferably, a single measurement step is carried out. At step 604, angles of the k joints can be provided, for example from a memory storing all n angles. At step 618, angles of the n joints can be provided, example from a memory storing all n angles.

There are different ways in which the desired joint angles for the n joints can be determined. One way is to determine the Jacobian matrix of all n joints (e.g. at step 616). Once the Jacobian matrix for all n joints has been determined, drive signals for the n joints can be calculated (620). The Jacobian matrix for the n joints takes account of the desired position of the attachment for the instrument (which can be based on a commanded position or movement input from a surgeon console) and the determined adjustment signal (which can be based on the defined constraint criteria).

Another way to determine the desired joint angles for the n joints is to determine the Jacobian matrix for k joints. This can be used to determine desired joint angles for the k joints. The desired joint angles for the remainder of the (n−k) joints can be directly calculated by making use of analytical solutions and trigonometry. An example will now be described, with k=4 and n=8. A solution for the angles of J1 to J4 is obtained, for example from the Jacobian, to calculate the pose after J4. This can define a reference frame for considering the angles of J5 to J8. In this example, J5 can be a proximal roll joint, J6 can be a pitch joint, J7 can be a yaw joint and J8 can be a distal roll joint. From a desired position/orientation of the attachment for the instrument, or of an instrument attached to the arm, a 'wrist bend angle' can be determined. This angle can be determined as the angle between the axis of rotation of J5 (which can be defined as a z-direction) and the direction of the instrument shaft, i.e. the direction p towards a point at the tip of the instrument. An angle, δ, can be determined as the angle between a projection of p onto the x-y plane and the y-axis. δ may be in the range ±90 degrees. The angle δ can be considered to be the angle that J5 will rotate through to align the overall wrist bend with the J7 (yaw) axis. The angle of J5 can be set as the angle δ. The angle of J5 can be selected as desired, and may be a constraint which enables the problem of J6, J7 and J8 to become well-determined. J6 and J7 can then be solved in any convenient way, based on the wrist bend angle and the angle δ. J8 may be determined to orient the instrument in a desired orientation.

The calculated drive signals are then used to drive one or more joints of the robot arm.

In the description above actions taken by the system have been split into functional blocks or modules for ease of explanation. In practice, two or more of these blocks could be architecturally combined. The functions could also be split into different functional blocks.

The present techniques have been described in the context of surgical robotic systems, though the features described below are not limited to such systems, but may be applied to robotic systems more generally. In some examples, the present techniques may be applied to robotic systems that operate remotely. Some examples of situations in which the present techniques may be useful include those that make use of 'snake-like' robots for exploration, investigation or repair. In the case of a surgical robot the end effector could be a surgical tool such as a scalpel, surgical cutter, surgical pincer or cauteriser.

Robotic systems can include manufacturing systems, such as vehicle manufacturing systems, parts handling systems, laboratory systems, and manipulators such as for hazardous materials or surgical manipulators.

The joints could be driven by electric motors, which could be rotary or linear, or by other means such as hydraulic or pneumatic actuators. These would be driven from the same control algorithms.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

What is claimed is:

1. A robotic system comprising:
   a robot having a base and an arm extending from the base to an attachment for an instrument, the arm comprising n joints, where n>1, whereby the configuration of the arm can be altered, the arm having a plurality of configurations for a given relationship between the base and the attachment for the instrument, the robot comprising a driver for each joint configured to drive the joint to move and a joint sensor for each joint for sensing a state of the joint; and
   a control unit configured to:
      obtain a desired position of the attachment for the instrument;
      for each of k joints where k<n, obtain a sensed joint state;
      compare the obtained k sensed joint states to a set of constraint criteria, the set of constraint criteria being indicative of the arm moving from a first configuration towards a second configuration, where movement of the arm is more constrained in the second configuration than in the first configuration;
      where the obtained k sensed joint states match the set of constraint criteria, determine a magnitude of an adjustment signal configured to slow, halt or reverse movement of the arm towards the second configuration;

using the desired position of the attachment for the instrument and the obtained k sensed joint states, determine a direction of the adjustment signal;

gate the adjustment signal in dependence on movement of the attachment for the instrument by modifying the adjustment signal with a gating gain derived from a speed associated with the arm;

for each of the n joints, obtain a sensed joint state;

using the desired position of the attachment for the instrument, the obtained n sensed joint states and the adjustment signal, determine a set of control signals for controlling the drivers; and drive the joints using the set of control signals.

2. A robotic system according to claim 1, in which the control unit is configured to determine the adjustment signal in dependence on one or more of: an instrument to be attached to the arm, a procedure that the arm is configured to perform, usage data gathered from system telemetry, and one or more algorithms for data analytics.

3. A robotic system according to claim 1, in which the set of constraint criteria comprises a range of values bounded by upper and lower threshold values, and the control unit is configured to determine that the k sensed joint states match the set of constraint criteria where the k sensed joint states comprise a value that equals one or other of the upper and lower threshold values or is between the upper and lower threshold values.

4. A robotic system according to claim 3, in which the control unit is configured to calculate a difference value from the difference between one of the k sensed joint state values and one or other of the upper and lower threshold values, and to determine the adjustment signal using the difference value.

5. A robotic system according to claim 4, in which determining the adjustment signal comprises applying a gain factor to the difference value.

6. A robotic system according to claim 5, in which the gain factor is selected in dependence on one or more of the characteristics of the arm, an instrument to be attached to the arm, the environment of the arm, and the procedure that the arm is used to perform.

7. A robotic system according to claim 1, in which the set of constraint criteria comprises a plurality of ranges of values, in respect of a plurality of joints, bounded by respective upper and lower threshold values, and the control unit is configured to determine that the k sensed joint states match the set of constraint criteria where respective sensed joint states comprise values that equal one or other of the respective upper and lower threshold values or are between the respective upper and lower threshold values.

8. A robotic system according to claim 1, in which the adjustment signal is configured to adjust a plurality of joints of the arm, and/or in which the adjustment signal comprises a joint speed signal.

9. A robotic system according to claim 1, in which the second configuration is relatively more constrained due to one or more of:

limiting a range of motion about a joint;
approaching or causing a joint singularity;
approaching a joint rotation limit of a joint; and
proximity of the arm to a person and/or an object.

10. A robotic system according to claim 1, in which the control unit is configured to dynamically modify the set of constraint criteria and/or the gain factor.

11. A robotic system according to claim 1, in which the state of a joint comprises one or more of an angle of that joint, a position of that joint, a speed or velocity of that joint, an acceleration of that joint, and a torque on or about that joint.

12. A robotic system according to claim 1, in which the control unit is configured to determine the adjustment signal such that the adjustment signal does not cause relative movement between the base and the attachment for the instrument, and/or in which the control unit is configured to determine the set of constraint criteria in dependence on an operating mode of the robotic system.

13. A robotic system according to claim 1, in which the control unit is configured to use the desired position of the attachment for the instrument and the obtained k sensed joint states to determine a solution for the k joints, and to use the solution for the k joints to determine the direction of the adjustment signal.

14. A robotic system according to claim 13, in which the control unit is configured to determine the solution for the k joints by using a least-squares method or variation thereof and determining a minimum norm solution for the k joints that lies within the nullspace.

15. A computer-implemented method of controlling a robotic system, the robotic system comprising a robot having a base and an arm extending from the base to an attachment for an instrument, the arm comprising n joints, where n>1, whereby the configuration of the arm can be altered, the arm having a plurality of configurations for a given relationship between the base and the attachment for the instrument, the robot comprising a driver for each joint configured to drive the joint to move and a joint sensor for each joint for sensing a state of the joint; the method comprising:

obtaining a desired position of the attachment for the instrument;

for each of k joints where k<n, obtaining a sensed joint state;

comparing the obtained k sensed joint states to a set of constraint criteria, the set of constraint criteria being indicative of the arm moving from a first configuration towards a second configuration, where movement of the arm is more constrained in the second configuration than in the first configuration;

where the obtained k sensed joint states match the set of constraint criteria, determining a magnitude of an adjustment signal configured to slow, halt or reverse movement of the arm towards the second configuration;

using the desired position of the attachment for the instrument and the obtained k sensed joint states, determining a direction of the adjustment signal;

gating the adjustment signal in dependence on movement of the attachment for the instrument by modifying the adjustment signal with a gating gain derived from a speed associated with the arm;

for each of the n joints, obtaining a sensed joint state;

using the desired position of the attachment for the instrument, the obtained n sensed joint states and the adjustment signal, determining a set of control signals for controlling the drivers; and driving the joints using the set of control signals.

16. A method according to claim 15, in which the method comprises determining the adjustment signal in dependence on one or more of: an instrument to be attached to the arm, a procedure that the arm is configured to perform, usage data gathered from system telemetry, and one or more algorithms for data analytics.

17. A method according to claim 15, in which the set of constraint criteria comprises a range of values bounded by upper and lower threshold values, and the method comprises determining that k sensed joint states match the set of constraint criteria where the k sensed joint states comprise a value that equals one or other of the upper and lower threshold values or is between the upper and lower threshold values.

18. A method according to claim 17, in which the method comprises calculating a difference value from the difference between one of the k sensed joint state values and one or other of the upper and lower threshold values, and determining the adjustment signal using the difference value.

19. A non-transitory computer readable storage medium having stored thereon computer readable instructions that, when executed at a computer system, cause the computer system to perform a method of controlling a robotic system, the robotic system comprising a robot having a base and an arm extending from the base to an attachment for an instrument, the arm comprising n joints, where n>1, whereby the configuration of the arm can be altered, the arm having a plurality of configurations for a given relationship between the base and the attachment for the instrument, the robot comprising a driver for each joint configured to drive the joint to move and a joint sensor for each joint for sensing a state of the joint; the method comprising:

obtaining a desired position of the attachment for the instrument;

for each of k joints where k<n, obtaining a sensed joint state;

comparing the obtained k sensed joint states to a set of constraint criteria, the set of constraint criteria being indicative of the arm moving from a first configuration towards a second configuration, where movement of the arm is more constrained in the second configuration than in the first configuration;

where the obtained k sensed joint states match the set of constraint criteria, determining a magnitude of an adjustment signal configured to slow, halt or reverse movement of the arm towards the second configuration;

using the desired position of the attachment for the instrument and the obtained k sensed joint states, determining a direction of the adjustment signal;

gating the adjustment signal in dependence on movement of the attachment for the instrument by modifying the adjustment signal with a gating gain derived from a speed associated with the arm;

for each of the n joints, obtaining a sensed joint state;

using the desired position of the attachment for the instrument, the obtained n sensed joint states and the adjustment signal, determining a set of control signals for controlling the drivers; and driving the joints using the set of control signals.

* * * * *